(12) United States Patent
Lee et al.

(10) Patent No.: US 6,554,844 B2
(45) Date of Patent: Apr. 29, 2003

(54) SURGICAL INSTRUMENT

(75) Inventors: Woojin Lee, Hopkinton, MA (US); David L. Brock, Natick, MA (US)

(73) Assignee: endoVia Medical, Inc., Norwood, MA (US)

( * ) Notice: Subject to any disclaimer, the term of this patent is extended or adjusted under 35 U.S.C. 154(b) by 0 days.

(21) Appl. No.: 09/827,643

(22) Filed: Apr. 6, 2001

(65) Prior Publication Data

US 2002/0038116 A1 Mar. 28, 2002

Related U.S. Application Data

(63) Continuation-in-part of application No. PCT/US00/12553, filed on May 9, 2000, and a continuation-in-part of application No. 09/746,853, filed on Dec. 21, 2000, which is a division of application No. 09/028,550, filed on Feb. 24, 1998, and a division of application No. 09/375,666, filed on Aug. 17, 1999, and a division of application No. 09/783,637, filed on Feb. 14, 2001.

(60) Provisional application No. 60/279,087, filed on Mar. 27, 2001, provisional application No. 60/269,203, filed on Feb. 15, 2001, provisional application No. 60/269,200, filed on Feb. 15, 2001, provisional application No. 60/276,151, filed on Mar. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/257,816, filed on Dec. 21, 2000, provisional application No. 60/257,868, filed on Dec. 21, 2000, provisional application No. 60/257,867, filed on Dec. 21, 2000, provisional application No. 60/257,869, filed on Dec. 21, 2000, provisional application No. 60/195,264, filed on Apr. 7, 2000, and provisional application No. 60/133,407, filed on May 10, 1999.

(51) Int. Cl.$^7$ ............................................. A61B 19/00
(52) U.S. Cl. ........................... 606/130; 606/205; 606/1
(58) Field of Search .................. 606/1, 130, 205; 600/102, 117, 118, 427, 429, 407; 414/5, 730; 901/2, 9, 25, 33

(56) References Cited

U.S. PATENT DOCUMENTS

| | | | |
|---|---|---|---|
| 4,218,173 A | | 8/1980 | Coindet et al. |
| 4,259,876 A | | 4/1981 | Belyanin et al. |
| 4,806,066 A | | 2/1989 | Rhodes et al. |
| 4,854,808 A | | 8/1989 | Bruno |
| 4,967,126 A | | 10/1990 | Gretz et al. |
| 5,038,089 A | | 8/1991 | Szakaly |
| 5,193,963 A | | 3/1993 | McAffee et al. |
| 5,382,885 A | | 1/1995 | Salcudean et al. |
| 5,397,323 A | | 3/1995 | Taylor et al. |
| 5,625,576 A | | 4/1997 | Massie et al. |
| 5,784,542 A | * | 7/1998 | Ohm et al. .................. 700/247 |
| 5,792,135 A | * | 8/1998 | Madhani et al. ................ 606/1 |
| 5,876,325 A | * | 3/1999 | Mizuno et al. ............. 600/102 |
| 6,206,903 B1 | | 3/2001 | Ramans |
| 6,223,100 B1 | * | 4/2001 | Green ........................ 600/109 |
| 6,312,435 B1 | | 11/2001 | Wallace et al. |
| 6,394,998 B1 | * | 5/2002 | Wallace et al. |

* cited by examiner

Primary Examiner—Pedro Philogene
(74) Attorney, Agent, or Firm—Hamilton, Brook, Smith & Reynolds, P.C.

(57) ABSTRACT

A surgical instrument end effector apparatus that includes a pair of jaws, a first pivot for supporting one of the jaws, a link member connected to one of the jaws, and a second pivot for supporting the link member. The link member has a first unlocked position in which one jaw member is opened relative to the other jaw member, and a second locked position in which one jaw member is locked closed relative to the other jaw member.

82 Claims, 5 Drawing Sheets

SURGICAL INSTRUMENT

RELATED APPLICATIONS

This application is a continuation-in-part of (and claims priority under 35 U.S.C. Sections 119 and 120, to the extent applicable, to) PCT application Ser. No. PCT/US00/12553 filed May 9, 2000, of U.S. application Ser. No. 09/746,853 filed Dec. 21, 2000 which is a division of U.S. application Ser. No. 09/028,550 filed Feb. 24, 1998 and U.S. application Ser. No. 09/375,666 filed Aug. 17, 1999 and U.S. application Ser. No. 09/783,637 filed Feb. 14, 2001.

This application also claims priority under 35 U.S.C. Sections 119 and 120 to the extent applicable to: U.S. Provisional Application Serial No. 60/279,087 for a SURGICAL INSTRUMENT filed Mar. 27, 2001, U.S. Provisional Application Serial No. 60/269,203 filed Feb. 15, 2001, U.S. Provisional Application Serial No. 60/269,200 filed Feb. 15, 2001, U.S. Provisional Application Serial No. 60/276,151 filed Mar. 15, 2001, U.S. Provisional Application Serial No. 60/276,217 filed Mar. 15, 2001, U.S. Provisional Application Serial No. 60/276,086 filed Mar. 15, 2001, U.S. Provisional Application Serial No. 60/276,152 filed Mar. 15, 2001, U.S. Provisional Application Serial No. 60/257,816 filed Dec. 21, 2000, U.S. Provisional Application Serial No. 60/257,868 filed Dec. 21, 2000; U.S. Provisional Application Serial No. 60/257,867 filed Dec. 21, 2000, U.S. Provisional Application Serial No. 60/257,869 filed Dec. 21, 2000; U.S. Provisional Application Serial No. 60/195,264 filed Apr. 7, 2000, U.S. Provisional Application Serial No. 60/133,407 filed May 10, 1999, and U.S. Application Serial No. 09/783,637 filed Feb. 14, 2001.

This disclosures of all of the foregoing applications and U.S. Pat. No. 6,197,017 are all incorporated herein by reference in their entirety.

BACKGROUND OF THE INVENTION

The present invention relates in general to surgical instruments and pertains, more particularly, to an improved jaw construction for a surgical instrument. The present invention also relates to a robotic medical system including master and slave stations, and an improved construction at the slave station.

One form of surgical instrument such as a laparoscopic instrument employs gripping jaws. These gripping jaws are limited as to the force that they can apply, particularly in telerobotic systems. This is due primarily to their small size and complex transmission mechanics, which restrict linkage size and maximum strength. However, rather than simply increasing, for example, cable tension, it is an objective of the present invention to provide an improved gripping mechanism that is operable without requiring large transmission forces.

Accordingly, it is an object of the present invention to provide a gripping mechanism that may be used for an articulated laparoscopic instrument and which dramatically increases grasp strength with minimum transmission force.

SUMMARY OF THE INVENTION

To accomplish the foregoing and other objects of this invention, there is provided a robotic medical system that is comprised of a master station including an input device, a slave station at which is disposed a surgical instrument, and a controller coupled between the master station and the slave station and for receiving a command from the input device for controlling the movement of the surgical instrument. The surgical instrument includes a pair of jaw members, a first pivot for supporting the pair of jaw members, and a link member connected to one of the jaw members. A second pivot is provided for supporting the link member. The link member has a first unlocked position in which on jaw member is open relative to the other jaw member, and a second locked position in which the one jaw member is locked closed relative to the other jaw member.

In accordance with further aspects of the present invention the first pivot may support the jaw members at a common first axis. Also included is a rotatable member, and a third pivot for supporting the rotatable member. The link member has one and other ends and the second pivot supports the one end of the link member from the rotatable member. There may also be included a fourth pivot for supporting the other end of the link member from the one jaw. The one jaw may have a leg that extends into a recess in the other jaw member where the first pivot holds the leg in the recess with limited rotational pivoting enabled by the first pivot. Both the jaw members may include gripper ends.

In accordance with still further aspects of the present invention there may be provided a first rotatable member and a second rotatable member. There may also be provided a first cable secured to the first rotatable member rotating the first rotatable member in either clockwise or counterclockwise directions. The jaw members are preferably disposed, in their locked position, with the second, third, and fourth pivots disposed in a single plane. The first pivot is preferably disposed outside of this single plane. There may also be provided a second rotatable member for fixedly supporting the other jaw member. Both the first and second rotatable members are supported at a common third pivot. A second cable is secured to the second rotatable member for rotating the second rotatable member in either clockwise or counterclockwise directions.

In accordance with another aspect of the present invention there is provided a surgical instrument end effector apparatus, preferably controlled from mechanical cabling. This apparatus comprises a pair of jaw members, a first pivot for supporting the pair of jaw members, a link member connected to one of the jaw members, and a second pivot for supporting the link member. The link member has a first unlocked position in which the one jaw member is open relative to the other jaw member, and a second locked position in which the one jaw member is locked closed relative to the other jaw member.

In accordance with still further aspects of the present invention there may be provided a surgical instrument that comprises, an instrument body including, at a more proximal end, a rigid section, and, at a more distal end, a flexible section. A base is secured to the distal end of the flexible section. A first pivot rotatably supports one end of a link piece from the base and along a first pivot axis. A pair of jaws are provided along with a second pivot for rotatably supporting the jaws from another end of the link piece and along a second pivot axis. The second pivot axis is disposed substantially orthogonal to the first pivot axis whereby the first and second pivot axes provide at least two degrees-of-freedom of the jaws.

BRIEF DESCRIPTION OF DRAWINGS

Numerous other objects, features and advantages of the invention should now become apparent upon a reading of the following detailed description as taken in conjunction with the accompanying drawings, in which.

DETAILED DESCRIPTION

Figure 1:
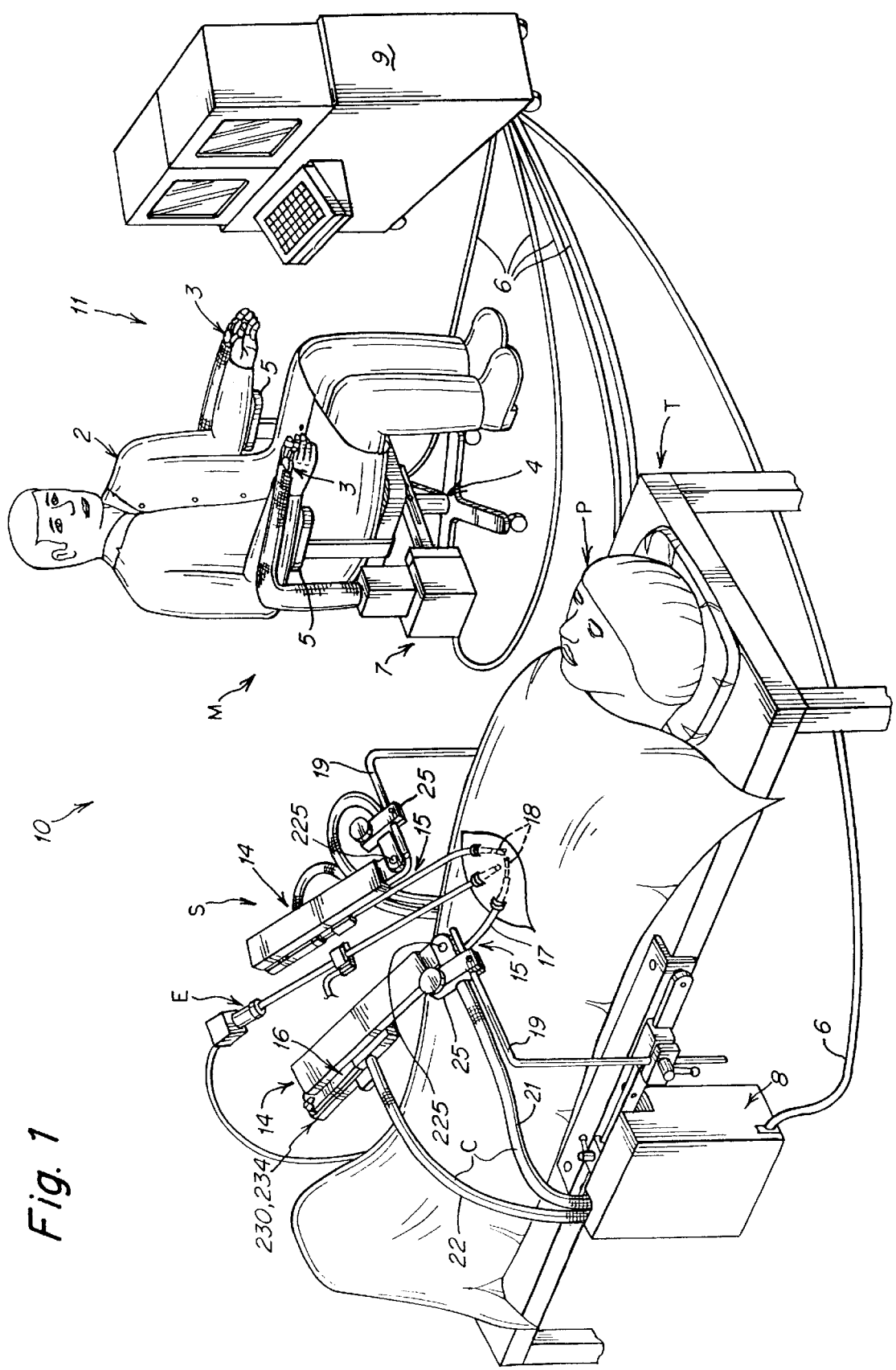
FIG. 1 is a perspective view illustrating a robotic system of the present invention.

Refer to FIG. 1 that illustrates a surgical robotic system. Although preferably used to perform minimally invasive surgery, it may also be used to perform other procedures as well, such as open or endoscopic surgical procedures. FIG. 1 illustrates a surgical instrument system 10 that includes a master station M at which a surgeon 2 manipulates an input device, and a slave station S at which is disposed a surgical instrument. In FIG. 1 the input device is illustrated at 3 being manipulated by the hand or hands of the surgeon. The surgeon is illustrated as seated in a comfortable chair 4. The forearms of the surgeon are typically resting upon armrests 5.

FIG. 1 illustrates a master assembly 7 associated with the master station M and a slave assembly 8 associated with the slave station S. Assembly 8 may also be referred to as a drive unit. Assemblies 7 and 8 are interconnected by means of cabling 6 with a controller 9. As illustrated in FIG. 1, controller 9 typically has associated therewith one or more displays and a keyboard.

As noted in FIG. 1, the drive unit 8 is remote from the operative site and is preferably positioned a distance away from the sterile field. The drive unit 8 is controlled by a computer system, part of the controller 9. The master station M may also be referred to as a user interface vis-á-vis the controller 9. Commands issued at the user interface are translated by the computer into an electronically drive motion in the drive unit 8. The surgical instrument, which is tethered to the drive unit through the cabling connections, produces the desired replicated motion FIG. 1, of course, also illustrates an operating table T upon which is placed the patient P.

Thus, the controller couples between the master station M and the slave station S and is operated in accordance with a computer algorithm, to be described in further detail hereinafter. The controller receives a command from the input device 3 and controls the movement of the surgical instrument so as to replicate the input manipulation.

Now, with further reference to FIG. 1, associated with the patient P is the surgical instrument 14, which in the illustrated embodiment actually comprises two separate instruments one on either side of an endoscope E. The endoscope includes a camera to remotely view the operative site. The camera may be mounted on the distal end of the instrument insert, or may be positioned away from the site to provide additional perspective on the surgical operation. In certain situations, it may be desirable to provide the endoscope through an opening other than the one used by the surgical instrument 14. In this regard, in FIG. 1 three separate incisions are shown, two for accommodating the surgical instruments and a centrally disposed incision that accommodates the viewing endoscope.

The surgical instrument 14 is generally comprised of two basic components including a surgical adaptor or guide 15 and an instrument insert or member 16. FIG. 1 illustrates the surgical adaptor 15. In FIG. 1 the instrument member 16 is not clearly illustrated but would extend through the adaptor 15. The instrument insert carries at its distal end the end effector. Descriptions of the surgical instrument are found hereinafter in additional drawings. The surgical adaptor 15 is basically a passive mechanical device, driven by the attached cable array.

In FIG. 1 there is illustrated cabling C coupling from the instrument 14 to the drive unit 8. The cabling C is preferably detachable from the drive unit 8. Furthermore, the surgical adaptor 15 may be of relatively simple construction. It may thus be designed for particular surgical applications such as abdominal, cardiac, spinal, arthroscopic, sinus, neural, etc. As indicated previously, the instrument insert 16 couples to the adaptor 15 and essentially provides a means for exchanging the instrument end effectors. The end effectors may include, for example, forceps, scissors, needle drivers, electrocautery etc.

Referring still to FIG. 1, the surgical system 10 may preferably be used to perform minimally invasive procedures, although it is to be understood that the system may also be used to perform other procedures, such as open or endoscopic surgical procedures. The system 10 includes a surgeon's interface 11, computation system or controller 9, drive unit 8 and the surgical instrument 14. The surgical instrument 14, as mentioned previously is comprised of an adaptor or guide 15 and the instrument insert or member 16. The system is used by positioning an end effector 18 of the instrument insert, which is inserted through the surgical adaptor or guide 15. During use, a surgeon may manipulate the input device 3 at the surgeon's interface 11 to effect desired motion of the end effector 18 within the patient. The movement of the handle or hand assembly at input device 3 is interpreted by the controller 9 to control the movement of the end effector 18.

The surgical instrument 14 is preferably mounted to a rigid post 19 which is illustrated in FIG. 1 as removably affixed to the surgical table T. This mounting arrangement permits the instrument to remain fixed relative to the patient even if the table is repositioned. In accordance with the present invention the concepts can be practiced even with a single surgical instrument, although, in FIG. 1 there is illustrated two such instruments.

As indicated previously, connecting between the surgical instrument 15 and the drive unit 8, are cablings C. These include two mechanical cable-in-conduit bundles 21 and 22. These cable bundles 21 and 22 may terminate at two connection modules, not illustrated in FIG. 1, which removably attach to the drive unit 8. For further details of the illustrated in FIG. 1, which removably attach to the drive unit 8. For further details of the connection modules 23 and 24 refer to earlier co-pending application No. PCT/US00/12553 Filed May 9, 2000. Although two cable bundles are described here, it is to be understood that more or fewer cable bundles may be used. Also, the drive unit 8 is preferably located outside the sterile field, although it may be draped with a sterile barrier so that it may be operated within the sterile field.

In the preferred technique for setting up the system, and with reference to FIG. 1, the surgical instrument 14 is inserted into the patient through an incision or opening. The instrument 14 is then mounted to the rigid post 19 using a mounting bracket 25. The cable bundles 21 and 22 are then passed away from the operative area to the drive unit 8. The connection modules of the cable bundles are then engaged into the drive unit 8. Instrument inserts 16 may then be passed through the surgical adaptor 15. The surgical inserts 16 are coupled laterally with the surgical adaptor 15 through an adaptor coupler, as described in further detail hereinafter.

The instrument 14 is controlled by the input device 3, which is be manipulated by the surgeon. Movement of the hand assembly produces proportional movement of the instrument 14 through the coordinating action of the controller 9. It is typical for the movement of a single handle control to control movement of a single instrument. However, FIG. 1 shows a second input device that is used to control an additional instrument. Accordingly, in FIG. 1 two input devices are illustrated and two corresponding instruments.

The surgeon's interface 11 is in electrical communication with the controller 9. This electrical control is primarily by way of the cabling 6 illustrated in FIG. 1 coupling from the bottom of the master assembly 7. Cabling 6 also couples from the controller 9 to the actuation or drive unit 8. This cabling 6 is electrical cabling. The actuation or drive unit 8, however, is in mechanical communication with the instrument 14. The mechanical communication with the instrument allows the electromechancial components to be removed from the operative region, and preferably from the sterile field. The surgical instrument 14 provides a number of independent motions, or degrees-of-freedom, to the end effector 18. These degrees-of-freedom are provided by both the surgical adaptor 15 and the instrument insert 16.

Figure 2:
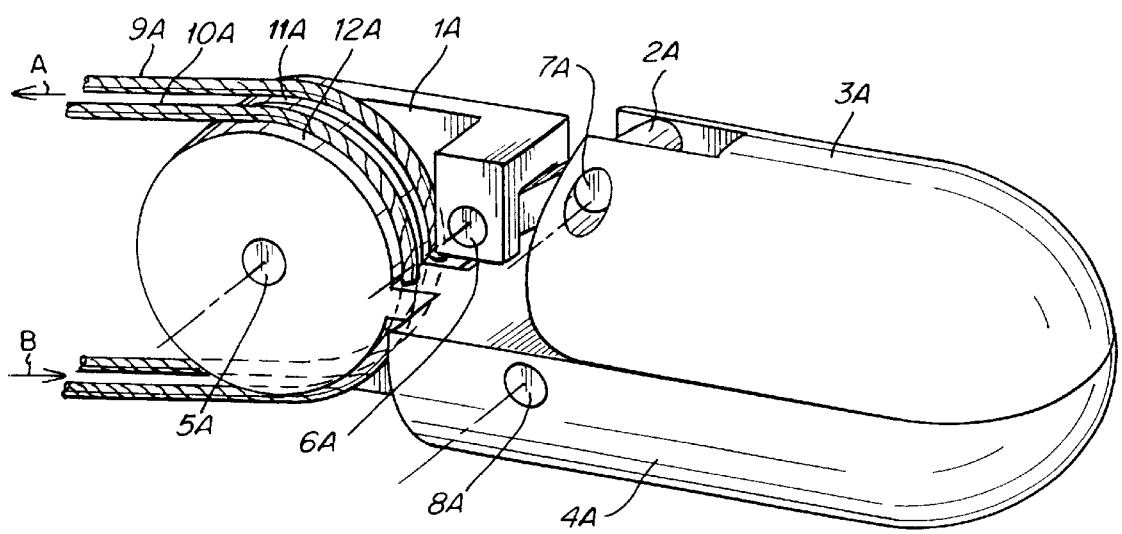
FIG. 2 is a perspective view showing a gripping mechanism as in accordance with the surgical instrument of the present invention.

Reference is now made to FIG. 2 for an illustration of a preferred gripping mechanism in accordance with the present invention. This mechanism includes four rigid cable 9A linkages 1A–4A, connected by revolute joints 5A–8A. A cable 9A wraps around and is affixed to capstan (rotatable member) 11A. If cable 9A is pulled in one direction this rotates the capstan and accordingly rotates linkage 1A in one direction. This direction is clockwise. Tension on the other end of the cable in the opposite direction causes counter-clockwise rotation of the linkage 1A. In FIG. 2 refer to the different direction arrows A and B.

In FIG. 2, counterclockwise rotation of linkage 1A, moves linkage 2A, which is rotationally connected to linkage 1A. Linkage 2A is also rotationally coupled to linkage 3A at joint 7A. Linkage 3A is also rotationally coupled to linkage 4A, which forms the lower, opposing jaw of the gripper. Continued counterclockwise rotation of linkage 1A,, and resultant movement of linkage 2A, eventually rotates linkage 3A counterclockwise about joint 8, thus opening the jaws.

With reference to FIG. 2, clockwise rotation of linkage 1A moves linkage 2A, which results in a corresponding clockwise rotation of linkage 3A. This effectively closes the jaws of the gripper. Rotating linkage 1A opens and closes the upper jaw (linkage) 3, but not in a proportional manner.

As noted in FIG. 2, the joints or pivot pins, 5A, 6A and 7A are essentially collinear when the mechanism is closed as in the position of FIG. 2. In other words, these pivot pins are essentially all in the same plane. The rotation of linkage 3A about joint 8A, results in essentially compression of linkage 2A rather than rotation. This effectively locks the jaw (linkage) 3A in place.

Thus, in connection with the perspective view of FIG. 2, if the jaws were to grasp a needle or suture, the needle or suture would be firmly held and unable to move within the gripping jaws. The combination of cable and linkage transmissions in this case greatly increases the effectiveness of the laporoscopic instrument.

Figure 3A:
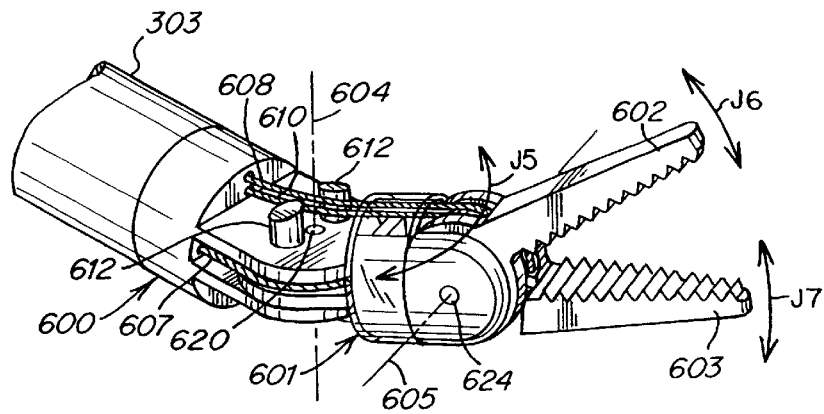
FIG. 3A is a perspective view at the end effector for one embodiment of gripping mechanism in accordance with the present invention.
Figure 3B:
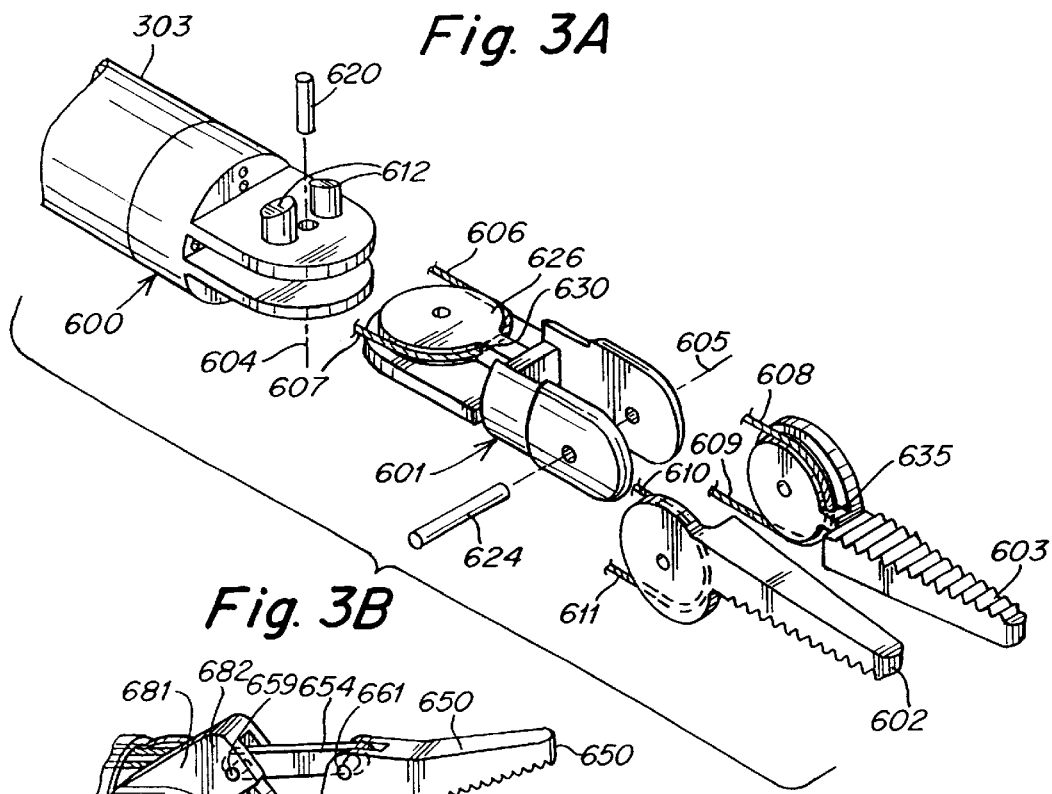
FIG. 3B is an exploded perspective view of the end effector of FIG. 16A.

The construction of one form of end effector is illustrated in FIGS. 3A and 3B. FIG. 3A is a perspective view while FIG. 3B is an exploded view. The end effector 18 is comprised of four members including the base 600, link 601, upper grip of jaw 602 and lower grip or jaw 603. The base 600 is affixed to the flexible stem section 303. As illustrated in the drawings, this flexible section may be constructed of a ribbed plastic. This flexible section is used so that the instrument will readily bend through the curved actuator tube 17.

The link 601 is rotatably connected to the base 600 about axis 604. FIG. 3B illustrates a pivot pin at 620. The upper and lower jaws 602 and 603 are rotatably connected to the link about axis 605, where axis 605 is essentially perpendicular to axis 604. FIG. 3B illustrates another pivot pin at 624.

Six cables 606–611, shown schematically in FIG. 3A and FIG. 3B, actuate the four members 600–603 of the end effector. Cable 606 travels through the insert stem (section 303) and through a hole in the base 600, wraps around curved surface 626 on link 601, and then attaches on link 601 at 630. Tension on cable 606 rotates the link 601, and attached upper and lower grips 602 and 603, about axis 604. Cable 607 provides the opposing action to cable 606, and goes through the same routing pathway, but on the opposite sides of the insert. Cable 607 may also attach to link 601 generally at 630.

Cables 608 and 610 also travel through the stem 302, 303 and though holes in the base 600. The cables 608 and 610 then pass between two fixed posts 612. These posts constrain the cables to pass substantially through the axis 604, which defines rotation of the link 601. This construction essentially allows free rotation of the link 601 with minimal length changes in cables 608–611. In other words, the cables 608–611, which actuate the grips 602 and 623, are essentially decoupled from the motion of link 601. Cables 608 and 610 pass over rounded sections and terminate on grips 602 and 603, respectively. Tension on cables 608 and 610 rotate grips 602 and 603 counter-clockwise about axis 605. Finally, as shown in FIG. 3B, the cables 609 and 611 pass through the same routing pathway as cables 608 and 610, but on the opposite side of the instrument. These cables 609 and 611 provide the clockwise motion to grips or jaws 602 and 603, respectively. At the jaws 602 and 603, as depicted in FIG. 3B, the ends of cable 608–611 may be secured at 635. The may occur with the use of an adhesive such as epoxy glue or the cables could be crimped to the jaw.

The instrument 16 slides through the guide tube 17 of adaptor 15, and laterally engages the adaptor coupler 230. The adaptor coupler 230 is pivotally mounted to the base piece 234. The base piece 234 rotationally mounts the guide tube 17. The base piece 234 is affixed to the linear slider or carriage assembly. The carriage assembly in turn is pivotally mounted at the pivot 225.

Figure 3C:
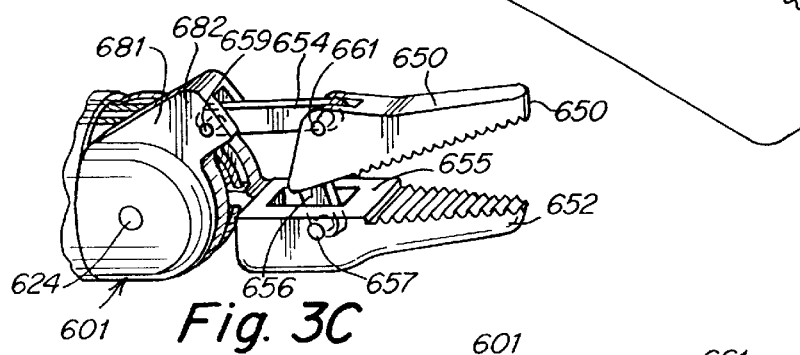
FIG. 3C is a perspective view of another version in accordance with the present invention.
Figure 3D:
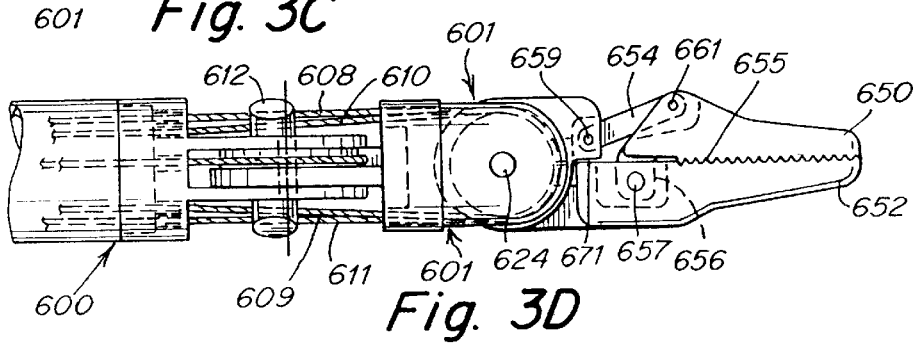
FIG. 3D is a side elevation view of the gripping mechanism of FIG. 3C.

Reference is now made to FIGS 3C and 3D. FIG. 3C is a fragmentary perspective view of an alternate form of set of jaws. These may be referred to as needle drivers. FIG. 3D is a side elevation view of the needle driver. The particular embodiment illustrated in FIGS. 3C and 3D employs an over-center camming arrangement so that the jaw is, not only closed, but also is a forced closure.

In FIGS. 3C and 3D, similar reference characters are employed with respect to the embodiment of the invention illustrated in FIGS. 3A and 3B. Thus, there is provided a base 600, a link 601, an upper jaw 650 and a lower jaw 652. The base 600 would be affixed to the flexible stem section 303. FIG. 3D also illustrates the sets of cables 608 and 610 on the top, and on the bottom are cables 609 and 611. This is cabling for operating the end jaws.

FIGS. 3C and 3D also illustrate linkages 654 and 656. It is the use of these linkages that provide the over-center camming operation.

As noted in, for example, FIG. 3C, the linkage 656 is actually fixed to the upper jaw 650 but pivots at a pin at the bottom thereof, within the recess in the lower jaw 652. This lower pivot pin is shown at 657.

Thus, with regard to FIGS. 3C and 3D there is a first pivot represented by pin 657, a second pivot represented by pin 659, a third pivot represented by pivot pin 624 and a fourth pivot represented by pin 661.

Figure 5A:
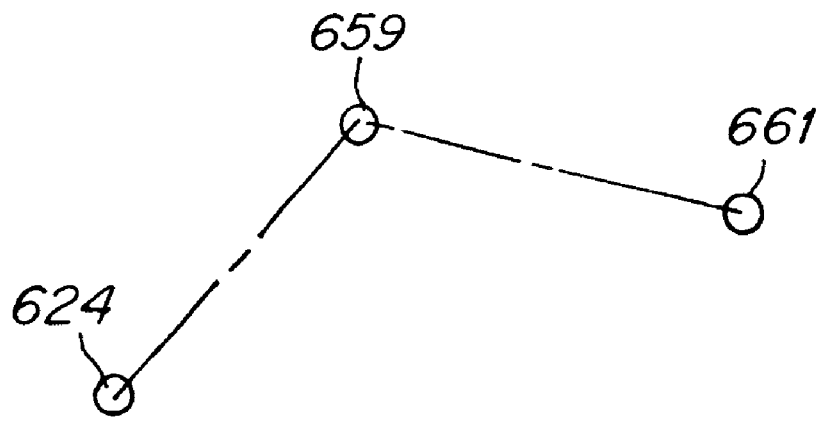
FIG. 5A–5C schematically illustrate pivots of the device for different positions thereof.

Now, with reference to FIGS. 3C and 3D it is noted that in FIG. 3C the jaws are shown in a substantially opened position, while in FIG. third pivot. 3D the jaws are shown in a closed position. In the fully open position of the jaws, the linkage 654 has its shown in a closed position. In the fully open position of the jaws, the linkage 654 has its pivot pin 661 at a lower position relative to the jaw 652, than the pivot pin 659. Refer also to the schematic diagram of FIG. 5A that illustrates pivots 624, 659 and 661. Note that pin 659 is above any plane that could be formed between pins 624 and 661. In FIG. 3C refer to the relatively flat but ridged surface 655.

Figure 5B:
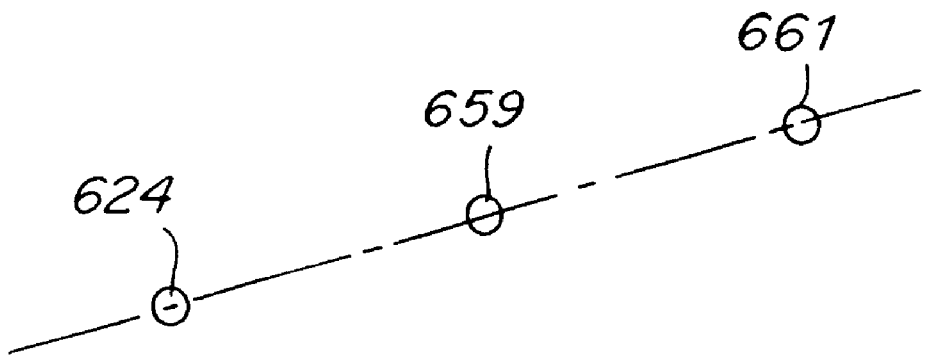

When the jaw 650 is closed, the linkage 654 moves toward the position shown in FIG. 3D where the pivots 624, 659, and 661 are essentially collinear or may be considered as in the same plane. However, before reaching the position shown in FIG. 3D, the jaws may be considered as grasping a needle, suture or even human tissue. At that position the linkage 654 is substantially parallel to the surface 655 of the lower jaw 652. Refer to FIG. 5B that illustrates this planar relationship of pivots 624, 659 and 661.

Figure 5C:
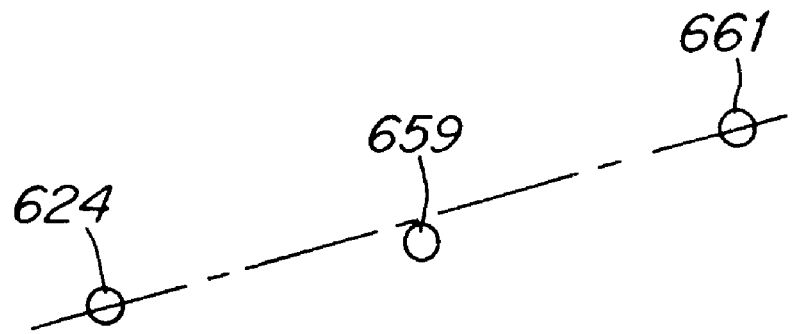

Further closure of the jaw 650 by way of the linkage 654, causes an over-camming action where the linkage 654 is locked down and the edge 671 butts up against the lower jaw 652. This action causes the pivot 659 to actually go beyond the plane defined by pivots 642, 659 and 661 to a locked position. In that locked position, if one were to draw a line between the pivots 624 and 661, one would find that the pivot 659 is slightly below the interconnecting line, thus forming a locking arrangement for the upper jaw 650 relative to the lower jaw 652 (see FIG. 5C).

In the embodiment of the invention illustrated in FIGS. 3A and 3B, the aforementioned cabling, connects directly to the jaws. However, in the embodiment of FIGS. 3C and 3D, one of the sets of cables couples to the lower jaw while the other set of cables couples to the rotating member 681. It is from the extension 682 of the rotating member 681, that the pivot pin 659 supports one end of the linkage 654. In this way, any rotation of the rotatable member 681 is translated through the linkage 654 to the upper jaw 650. Refer in particular to FIG. 3C.

Figure 4:
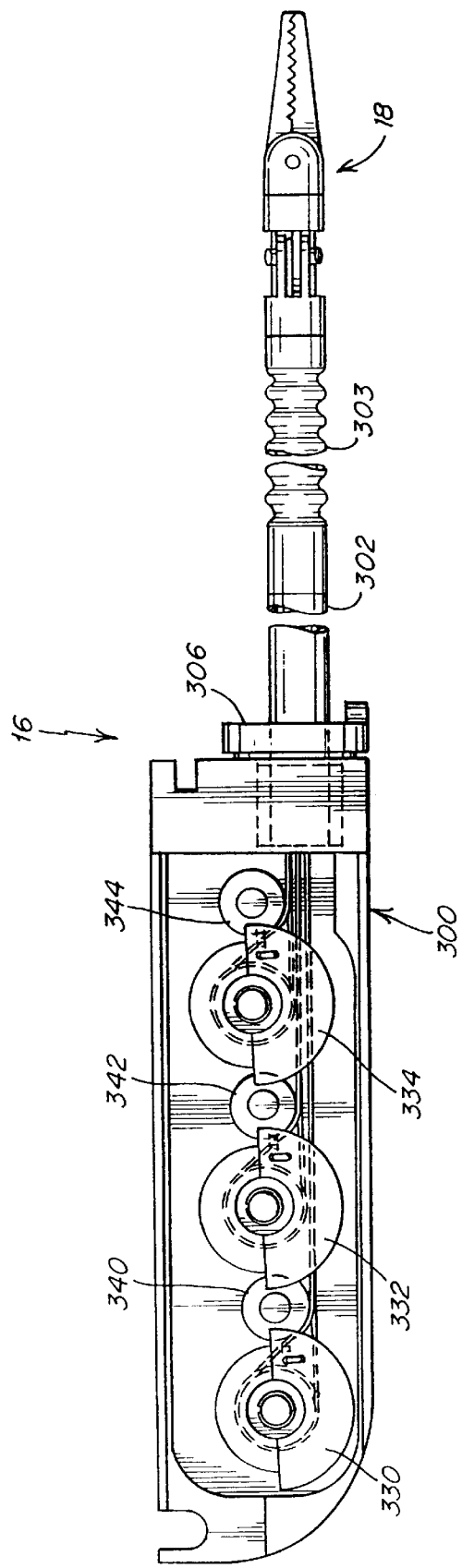
FIG. 4 is a top plan view of a complete detachable instrument member or insert as in accordance with the present invention.

FIG. 4 is a plan view showing an instrument including the end effector 18, and elongated sections including a rigid section 302 and a flexible section 303. At the end of the flexible stem section 303, is the end effector 18. The coupler 300 includes one or more wheels which laterally engage wheels of the coupler associated with the surgical adaptor. The coupler 300 also includes an axial wheel 306 which also engages a wheel on the adaptor. The axial engagement wheel 306 is fixed to the rigid stem 302, and is used to rotate the end effector axially at the distal end of the flexible stem section 303.

FIG. 4 illustrates the base 300 of the instrument 16 with wheels that have half-moon construction for engagement with wheels of the adaptor. FIG. 4 shows three wheels 320, 332, and 334. These wheels are meant to mate with the corresponding wheels of the adaptor. Also illustrated in FIG. 4 are capstans or idler pulleys 340, 342, and 344 associated, respectively, with wheels 330, 332, and 334.

Each wheel of the coupler has two cables that are affixed to the wheel and wrapped about opposite sides at its base. The lower cable rides over one of the idler pulleys or capstans, which routes the cables toward the center of the instrument stem 302. It is desirable to maintain the cables near the center of the instrument stem. The closer the cables are to the central axis of the stem, the less disturbance motion on the cables. The cables may then be routed through plastic tubes that are affixed to the proximal end of the rigid stem 302 and the distal end of the flexible stem section 303. The tubes maintain constant length pathways for the cables as they move within the instrument stem.

Regarding the coupler 300, there are six cables that connect to each of the wheels. Two cables connect to each wheel and one of these cables extend about the associated idler pulley or capstan. These are illustrated in FIG. 4 as idler pulleys 340, 342 and 344. Thus, six separate cables extend through the rigid stem 302 and down through the flexible stem section 303 to the end effector area.

Thus, associated with the wheels 330, 332, and 334, there are six cable lengths that extend through the sections 302 and 303. These six cables lengths are illustrated, for example, in FIG. 3D. One set of these cables controls the pivoting, such as the pivoting about pin 620. The other cables 608–611 control the operation at the gripping jaws. For example, cables 608 and 609 may control the different direction movement of the lower jaw 652. The cables 610 and 611 may control the rotatable member 681 which in turn, through linkage 654, controls the opening and closing of the upper jaw 650.

Having now described the limited number of embodiments of the present invention, it should be apparent to those skilled in the art that numerous other embodiments and modifications thereof are contemplated as falling within the scope of the present invention, as defined by the appended claim.

What is claimed is:

1. A robotic medical system that is comprised of a master station including an input device, a slave station at which is disposed a surgical instrument, and a controller coupled between said master station and said slave station and for receiving a command from said input device for controlling the movement of said surgical instrument, said surgical instrument including, a pair of jaw members, a first pivot for supporting said pair of jaw members, a link member connected to only one of said jaw members, and a second pivot for supporting said link member, said link member having a first unlocked position in which the one jaw member is open relative to the other jaw member, and a second locked position in which the one jaw member is locked closed relative to the other jaw member.

2. A robotic medical system of claim 1 wherein said first pivot supports the jaw members at a common first axis.

3. A robotic medical system that is comprised of a master station including an input device, a slave station at which is disposed a surgical instrument, and a controller coupled between said master station and said slave station and for receiving a command from said input device for controlling the movement of said surgical instrument, said surgical instrument including, a pair of jaw members, a first pivot for supporting said pair of jaw members, a link member connected to one of said jaw members, a second pivot for supporting said link member, said link member having a first unlocked position in which the one jaw member is open relative to the other jaw member, and a second locked position in which the one jaw member is locked closed relative to the other jaw member, wherein said first pivot supports the jaw members at a common first axis, a rotatable member, and a third pivot for supporting said rotatable member.

4. A robotic medical system of claim 3 wherein said link member has one and other ends and said second pivot supports the one end of said link member from said rotatable member.

5. A robotic medical system of claim 4 including a forth pivot for supporting the other end of the link member from said one jaw member.

6. A robotic medical system that is comprised of a master station including an input device, a slave station at which is disposed a surgical instrument, and a controller coupled between said master station and said slave station and for receiving a command from said input device for controlling the movement of said surgical instrument, said surgical instrument including, a pair of jaw members, a first pivot for supporting said pair of jaw members, a link member connected to one of said jaw members, a second pivot for supporting said link member, said link member having a first unlocked position in which the one jaw member is open relative to the other jaw member, and a second locked position in which the one jaw member is locked closed relative to the other jaw member, wherein said one jaw member has a leg that extends into a recess in the other jaw member.

7. A robotic medical system of claim 6 wherein both said jaw members include gripper end.

8. A robotic medical system of claim 7 wherein said first pivot holds said leg in said recess with limited rotational pivoting enabled by said first pivot.

9. A robotic medical system that is comprised of a master station including an input device, a slave station at which is disposed a surgical instrument, and a controller coupled between said master station and said slave station and for receiving a command from said input device for controlling the movement of said surgical instrument, said surgical instrument including, a pair of jaw members, a first pivot for supporting said pair of jaw members, a link member connected to one of said jaw members, a second pivot for supporting said link member, said link member having a first unlocked position in which the one jaw member is open relative to the other jaw member, and a second locked position in which the one jaw member is locked closed relative to the other jaw member, a first rotatable member, and a third pivot for supporting said first rotatable member.

10. A robotic medical system of claim 9 including a first cable secured to said first rotatable member for rotating said first rotatable member in one of clockwise and counter clockwise directions.

11. A robotic medical system of claim 10 wherein said link member has one and other ends and said second pivot supports the one end of said link member from first rotatable member.

12. A robotic medical system of claim 11 including a forth pivot for supporting the other end of the link member from said one jaw member.

13. A robotic medical system of claim 12 wherein, when said jaw members are in said locked position, said second, third and fourth pivots are disposed substantially in a single plane.

14. A robotic medical system of claim 13 wherein said fourth pivot is slightly below a lien joining the second and third pivots so as to provide a locking action by said jaw members.

15. A robotic medical system of claim 12 including a second rotatable member for fixedly supporting said other jaw member.

16. A robotic medical system of claim 15 wherein said first and second rotatable members are both supported at a common third pivot.

17. A robotic medical system of claim 16 including a second cable secured to said second rotatable member for rotating said second rotatable member in one of clockwise and counter clockwise directions.

18. A surgical instrument end effector apparatus controlled from mechanical cabling and comprising:
one and other jaw members;
a first pivot for supporting said pair of jaw members;
a link member connected to only one of said jaw members;
and a second pivot for supporting said link member;
said link member having a first unlocked position in which the one jaw member is open relative to the other jaw member; and a second locked position in which the one jaw member is locked closed relative to the other jaw member.

19. The surgical instrument of claim 18 wherein said first pivot supports the jaw members at a common first axis.

20. A surgical instrument end effector apparatus controlled from mechanical cabling and comprising:
one and other jaw members;
a first pivot for supporting said pair of jaw members;
a link member connected to one of said jaw members;
a second pivot for supporting said link member;
said link member having a first unlocked position in which the one jaw member is open relative to the other jaw member; and a second locked position in which the one jaw member is locked closed relative to the other jaw member, wherein said first pivot supports the jaw members at a common first axis;
a rotatable member, and a third pivot for supporting said rotatable member.

21. The surgical instrument of claim 20 wherein said link member has one and other ends and said second pivot supports the one end of said link member from said rotatable member.

22. The surgical instrument of claim 21 including a forth pivot for supporting the other end of the link member from said one jaw member.

23. A surgical instrument end effector apparatus controlled from mechanical cabling and comprising;
one and other jaw members;
a first pivot for supporting said pair of jaw members;
a link member connected to one of said jaw members;
a second pivot for supporting said link member;
said link member having a first unlocked position in which the one jaw member is open relative to the other jaw member; and a second locked position in which the one jaw member is locked closed relative to the other jaw member, wherein said one jaw member has a leg that extends into a recess in the other jaw member.

24. The surgical instrument of claim 23 wherein both said jaw members include gripper ends.

25. The surgical instrument of claim 24 wherein said first pivot holds said leg in said recess with limited rotational pivoting enabled by said first pivot.

26. A surgical instrument end effector apparatus controlled from mechanical cabling and comprising:
   one and other jaw members;
   a first pivot for supporting said pair of jaw members;
   a link member connected to one of said jaw members;
   a second pivot for supporting said link member;
   said link member having a first unlocked position in which the one jaw member is open relative to the other jaw member; and a second locked position in which the one jaw member is locked closed relative to the other jaw member;
   a first rotatable member, and a third pivot for supporting said first rotatable member.

27. The surgical instrument of claim 26, including a first cable secured to said first rotatable member for rotating said first rotatable member in one of clockwise and counter clockwise directions.

28. The surgical instrument of claim 27 wherein said link member has one and other ends and said second pivot supports the one end of said link member from first rotatable member.

29. The surgical instrument of claim 28 including a forth pivot for supporting the other end of the link member from said one jaw member.

30. The surgical instrument of claim 29 wherein, when said jaw members are in said locked position, said second, third and fourth pivots are disposed substantially in a single plane.

31. The surgical instrument of claim 30 wherein said fourth pivot is slightly below a line joining the second and third pivots so as to provide a locking action by said jaw members.

32. The surgical instrument of claim 29 including a second rotatable member for fixedly supporting said other jaw member.

33. The surgical instrument of claim 32 wherein said first and second rotatable members are both supported at a common third pivot.

34. The surgical instrument of claim 33 including a second cable secured to said second rotatable member for rotating said second rotatable member in one of clockwise and counter clockwise directions.

35. A surgical instrument comprising:
   an instrument body including at a more proximal end a rigid section, and at a more distal end a flexible section;
   a base secured to the distal end of the flexible section;
   a link piece;
   a first pivot for rotatably supporting one end of said link piece from said base and along a first pivot axis;
   a pair of jaws;
   a second pivot for rotatably supporting said jaws from another end of said link piece and along a second pivot axis;
   said second pivot axis being disposed substantially orthogonal to said first pivot axis;
   wherein said first and second pivot axes provide at least two degrees-of-freedom of said jaws;
   mechanical cabling intercoupling through said rigid and flexible sections and including at least one cable for coupling to said one end of said link piece for causing opposite direction rotation thereof;
   at least a second cable coupling to one jaw and at least a third cable coupling to the other jaw; and
   guide means for maintaining said second and third cables at a position over said first pivot.

36. A surgical instrument of claim 35 wherein said base includes a pair of spaced extensions with the one end of said link piece disposed between said spaced extensions.

37. A surgical instrument of claim 36 wherein said link piece at said one end includes an arcuate surface with said first cable secured at a position therealong.

38. A surgical instrument of claim 37 wherein each of said jaws include an arcuate surface with said second and third cables respectively secured therealong.

39. A surgical instrument of claim 38 wherein the other end of said link piece is forked to receive the arcuate portions of said jaws therebetween.

40. A medical instrument comprising:
   en elongated stem section having at its distal end a support base;
   a link having proximal and distal ends, said proximal end supported from said base for pivoting about a first axis;
   a tool supported from the distal end of said link for pivoting about a second pivot axis;
   at least one actuation cable extending through said elongated stem section and passing substantially through said first axis permitting actuation of said tool independent of any rotation of said link relative to said base about said first pivot axis.

41. The medical instrument of claim 40 wherein said tool comprises a pair of jaws and said at least one actuation cable comprises a pair of cables associated respectively with said pair of jaws.

42. The medical instrument of claim 40 wherein said elongated stem section includes a proximal rigid stem section and a distal flexible stem section.

43. The medical instrument of claim 40 wherein said second pivot axis is transverse to said first pivot axis.

44. The medical instrument of claim 40 including a further actuation cable for coupling to said link for controlling rotation of said link.

45. The medical instrument of claim 44 wherein operation of the further actuation cable controls rotation of the link with minimal length change in said at least one actuation cable.

46. The medical instrument of claim 40 including a mechanical coupler couplable to a drive unit and arranged at the proximal end of the elongated stem section.

47. The medical instrument of claim 40 wherein said tool comprises a pair of jaw members, a link member connected to one of said jaw members, and a further pivot for supporting said link member; said link member having a first unlocked position in which one jaw member is open relative to the other jaw member, and a second locked position in which one jaw member is locked closed relative to the other jaw member.

48. The medical instrument of claim 40 including a constraining member to constrain the placement of the at least one actuation cable to pass through said first pivot axis.

49. The medical instrument of claim 48 wherein said constraining member comprises a pair of posts on said base.

50. The medical instrument of claim 49 wherein there is a post on either side of the first pivot axis with the actuation cable confined between said posts.

51. A medical instrument comprising:

a pair of work members;

a pivot for intercoupling the work members so as to permit relative pivoting between open and closed positions thereof;

a rotatable member controlled from at least one mechanical cable that is adapted to operate at least one of said work members;

and a linkage operatively intercoupling the rotatable member and one of said work members for transferring mechanical action from the rotatable member to said one of said work members for facilitating at least closing thereof.

52. A medical instrument set forth in claim 51 wherein said pivot is about one axis and said rotatable member rotates about another axis different from the one axis.

53. A medical instrument as set forth in claim 51 wherein said linkage has one and another ends that pivot about respective linkage pivot axes that extend in parallel.

54. A medical instrument as set forth in claim 51 wherein said pivot is about a first axis, said linkage pivots at one end about a second axis, and said rotatable member pivots about a third axis.

55. A medical instrument as set forth in claim 51 wherein said working members are telerobotically controlled from a remote input device via an electrical controller.

56. A method of grasping an item by means of one and another work elements, comprising the steps of:

providing a pivot between the work elements so as to permit relative pivoting between open and closed positions thereof;

providing a rotatable mechanism coupled with said work elements, operated from at least one mechanical cable, and that is controlled to manipulate at least one of said work elements; and connecting a linkage between the rotatable mechanism and one of said work elements for transferring mechanical action from the rotatable mechanism, through said linkage, to functionally operate one of said work elements.

57. A method as set forth in claim 56 wherein said rotatable mechanism is operated from at least two cables for controlling respective work elements.

58. A method as set forth in claim 56 including controlling said work elements telerobotically from a remote input device via an electrical controller.

59. A method as set forth in claim 56 including providing said pivot about a first axis, said linkage at one end about a second axis, and said rotatable mechanism pivots about a third axis.

60. A method as set forth in claim 56 wherein the step of connecting the linkage includes pivoting opposite ends of the linkage about respective linkage pivot axes that extend in parallel.

61. A method as set forth in claim 56 wherein the step of providing a rotatable mechanism includes providing a first part that enables rotation of said another work element, and a second part that operates said linkage for providing locking action to said one work element.

62. A method as set forth in claim 51 wherein the step of providing a rotatable mechanism includes providing a rotatable assembly.

63. A robotic medical system comprising: a surgical instrument; an input device; and a controller coupled between said input device and surgical instrument for controlling the movement of said surgical instrument; said surgical instrument including, a pair of jaw members, a pivot for supporting said pair of jaw members so as to permit relative pivoting therebetween; a rotatable member supported about a second pivot and link member connected between said rotatable member and one of said pair of jaw members; said link member having one and another ends that pivot about respective axes that extend substantially in parallel.

64. A robotic medical system as set forth in claim 63 wherein said rotatable member is controlled from at least one mechanical cable that is adapted to operate at least one of said jaw members.

65. A robotic medical system as set forth in claim 64 wherein said pivot is about one axis and said rotatable member rotates about another axis different from the one axis.

66. A robotic medical system as set forth in claim 65 wherein said link member one end pivots from said rotatable member about a second axis, said rotatable member pivots about a third axis, and said link member another end pivots from said one jaw member about a fourth axis.

67. A robotic medical system as set forth in claim 66 wherein all said first, second, third, and fourth axes are disposed in parallel.

68. A robotic medical system as set forth in claim 67 wherein, in a locked position of the link member, the second axis is at a position just below a locus line joining the third and fourth axes.

69. A robotic medical system as set forth in claim 63 wherein the link member provides a locking cam action in a locked position thereof with the one end pivot of the link member providing an over-center locked action relation to the other end pivot.

70. In a medical instrument that has one and other work elements that are coupled from an instrument shaft base and controllable to orient the work elements in different positions; a locking apparatus that includes a linkage intercoupling the base and at least said one of said work elements, the other of said work elements being supported from said base, and mechanical cabling coupled to said base for respective control of said work elements including locking of said linkage in a cam locking position corresponding to a locked closed position of said work elements.

71. In a medical instrument as set forth in claim 70 including a rotatable member at said base, said linkage pivoted from said rotatable member at one end thereof.

72. In a medical instrument as set forth in claim 71 wherein said linkage has one and other ends that pivot about respective axes that extend substantially in parallel.

73. In a medical instrument as set forth in claim 70 including a pivot for supporting said work elements so as to permit relative pivoting therebetween.

74. In a medical instrument as set forth in claim 73 wherein said one work element has a leg that extends into a recess in the other work element.

75. In a medical instrument as set forth in claim 71 wherein said linkage has one and other ends that pivot about respective axes that are non-orthogonal.

76. In a medical instrument as set forth in claim 70 including an electrical controller for controlling said work elements telerobotically from a remote input device.

77. A medical instrument comprising:

a pair of work members;

a first pivot for intercoupling the work members so as to permit relative pivoting between open and closed positions thereof;

a rotatable member controlled from at least one mechanical cable that is adapted to operate at least one of said work members;

and a linkage operatively intercoupling the rotatable member and one of said work members;

said linkage defining a second pivot, displaced from said first pivot, for providing pivot support of said one work member.

78. A medical instrument as set forth in claim 77 including an electrical controller for controlling said work elements telerobotically from a remote input device.

79. A medical instrument as set forth in claim 77 wherein said second pivot is at one end of the linkage coupling the linkage to said one work member, and said linkage has another end pivotally connected to said rotatable member.

80. A medical instrument as set forth in claim 79 wherein said rotatable member is supported at a third pivot, separate from said first and second pivots.

81. A medical instrument as set forth in claim 80 wherein said first, second, and third pivots all extend in parallel.

82. A robotic medical system comprising: a medical instrument; an input device; and a controller coupled between said input device and medical instrument for controlling the movement of said medical instrument; said medical instrument including, a pair of jaw members, a pivot for supporting said pair of jaw members so as to permit relative pivoting therebetween; and a link means connected to only one of said jaw members; said link means having one and another ends that have defined thereat respective opposed pivot axes that extend substantially in parallel.

* * * * *

UNITED STATES PATENT AND TRADEMARK OFFICE
CERTIFICATE OF CORRECTION

PATENT NO. : 6,554,844 B2
DATED : April 29, 2003
INVENTOR(S) : Woojin Lee and David L. Brock It is certified that error appears in the above-identified patent and that said Letters Patent is hereby corrected as shown below:

Column 9,
Line 38, delete "end" and insert -- ends --;

Column 10,
Line 6, delete "lien" and insert -- line --;
Line 56, delete ";" and insert -- : --;

Column 11,
Line 63, delete "wherein" and insert -- whereby --;

Column 12,
Line 21, delete "en" and insert -- an --;

Column 13,
Line 14, insert -- as -- between "instrument" and "set";

Column 14,
Line 4, insert -- a -- between "and" and "link";
Line 32, delete "locked" and insert -- locking --;
Line 32, delete "relation" and insert -- relative --;

Column 15,
Line 4, delete "pivot" and insert -- pivotal --.

Signed and Sealed this

Nineteenth Day of August, 2003

JAMES E. ROGAN
*Director of the United States Patent and Trademark Office*